(12) United States Patent
Matsuoka et al.

(10) Patent No.: US 6,344,358 B1
(45) Date of Patent: Feb. 5, 2002

(54) AGENT FOR EXPRESSION OF LONG-TERM POTENTIATION OF SYNAPTIC TRANSMISSION COMPRISING COMPOUND HAVING BRAIN SOMATOSTATIN ACTIVATION PROPERTY

(75) Inventors: Nobuya Matsuoka, Ikoma; Masamichi Satoh, Kyoto, both of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/321,745

(22) Filed: May 28, 1999

(51) Int. Cl.$^7$ ................................................ G01N 33/48
(52) U.S. Cl. .................... 436/63; 514/740; 514/741; 424/520; 424/570
(58) Field of Search ............................ 436/63; 435/1.1; 514/740, 741; 424/520, 570

(56) References Cited

U.S. PATENT DOCUMENTS 5,250,528 A * 10/1993 Oku et al. .................. 514/252

FOREIGN PATENT DOCUMENTS

| EP | 0 436 734 | 7/1991 |
| WO | WO 98/25914 | 6/1998 |
| WO | WO 98/27930 | 7/1998 |

OTHER PUBLICATIONS

Matsuoka et al. *Brain Research*, vol. 553, pp. 188–194, 1991.*
Matsuoka et al. *Journal of Pharmacol. Exp. Ther.*, vol. 280, No. 3, pp. 1201–1209, 1997.*
Nobuya Matsuoka, et al., Brain Research, vol. 794, No. 2, pp. 248–254, "FK960, A Novel Potential Anti–Dementia Drug, Augments Long–Term Potentiation in Mossy Fiber–CA3 Pathway of Guinea–Pig Hippocampal slices", Jun. 1, 1998.
Abstracts, Society for Neuroscience, vol. 24, Part 1, p. 733, "FK960, A Potential Antidementia Drug, Augments the Long–Term Potentiation in Guinea–Pig Hippocampal Slices Through the Novel Mechanism which is Mediated by an Activation of Somatostatinergic Nervous System", Nov. 7–12, 1998.
Mayako Yamazaki, et al., The Journal of Pharmacology and Experimental Therapeutics, vol. 279, No. 3, pp. 1157–1173, FK960 N–(4–Acetyl–1–Piperazinyl)–P–Fluorobenzamide Monohydrate Ameliorates the Memory Deficits in Rats Through a Novel Mechanism of Action, Dec., 1996.
N. Matsuoka, et al., "Role of Somatostatin in the Augmentation of Hippocampal Long–Term Potentiation by FR121196, A Putative Cognitive Enhancer", *European Journal of Pharmacology*, Jun. 1993, vol. 241, pp. 27–34.

* cited by examiner

*Primary Examiner*—Maureen M. Wallenhorst
(74) *Attorney, Agent, or Firm*—Oblon, Spivak, McClelland, Maier & Neustadt, P.C.

(57) ABSTRACT

The present invention relates to an agent for the expression of long-term potentiation of synaptic transmission, which contains a compound having a brain somatostatin activation property as an active ingredient and to a screening method of an agent for the expression of long-term potentiation of synaptic transmission, which uses a soniatostatin releasing property as an index. The present invention is useful for the prophylaxis and/or treatment of cerebral diseases of dementia, amnesia, manic-depressive psychosis, schizophrenia, Parkinson's disease, psychosomatic disease and the like.

10 Claims, 4 Drawing Sheets

AGENT FOR EXPRESSION OF LONG-TERM POTENTIATION OF SYNAPTIC TRANSMISSION COMPRISING COMPOUND HAVING BRAIN SOMATOSTATIN ACTIVATION PROPERTY

TECHNICAL FIELD

The present invention relates to an agent for the expression of long-term potentiation of synaptic transmission, an anti-dementia agent and an anti-amnesia agent, all of which containing a compound having a brain somatostatin activation property. More particularly, the present invention relates to an agent for the expression of long-term potentiation of synaptic transmission, an anti-dementia agent and an anti-amnesia agent, all of which containing a compound exerting a brain somatostatin release promoting action through suppression of the negative feedback mechanism of brain somatostatin release. The present invention moreover relates to a method for expressing long-term potentiation of synaptic transmission, a method for the treatment and/or prophylaxis of dementia and amnesia, and a screening method of these drugs using a somatostatin releasing property as an index.

BACKGROUND ART

The hippocampal function is said to be responsible for learning and memory. When an input neuron of the hippocampus is stimulated for a short time at high frequency, the efficiency of synaptic transmission continues to increase for a long time thereafter. This phenomenon is called long-term potentiation (hereinafter also referred to as LTP) of synaptic transmission, and has been recognized as a cellular model of learning and memory (T. V. P. Bliss and G. L. Collingdidge, Nature vol. 361, p.31, 1993). There is a demand for further elucidation of the mechanism of the LTP and the relation thereof with learning and memory. Also, a search for a compound having a property of long-term potentiation of synaptic transmission has been desired.

Somatostatin has been known for quite a long time as a hypothalamic hormone capable of suppressing the secretion of somatotropin from the pituitary gland. It has been recently found that it is also present in the cerebral cortex and the hippocampus, that are important cerebral sites for memory and learning, at high concentrations, playing an important role in memory and learning as a neuromodulator.

SUMMARY OF THE INVENTION

As a result of the intensive studies of the present inventors, it has been newly found that a compound having a brain somatostatin release promotion property expresses long-term potentiation of synaptic transmission. Based on this new finding, we have found that administration of a compound having a brain somatostatin release promoting property leads to the prophylaxis and/or treatment of cerebral diseases such as dementia, amnesia, manic-depressive psychosis, schizophrenia, Parkinson's disease, psychosomatic disease, and the like, which resulted in the completion of the present invention.

Accordingly, the present invention provides the following.

(1) An agent for expression of long-term potentiation of synaptic transmission, which comprises a compound having a brain somatostatin activation property as an active ingredient.

(2) The agent for expression of long-term potentiation of synaptic transmission of (1), wherein the compound exerts an action to promote a release of brain somatostatin through suppression of a negative feedback mechanism of brain somatostatin release.

(3) The agent for expression of long-term potentiation of synaptic transmission of (1) or (2), which is an agent for the prophylaxis or treatment of cerebral diseases.

(4) The agent for expression of long-term potentiation of synaptic transmission of (3), which is an agent for the prophylaxis or treatment of dementia or amnesia.

(5) A method for expressing long-term potentiation of synaptic transmission, comprising administering an effective amount of a compound having a brain somatostatin activating property.

(6) The method for expressing long-term potentiation of synaptic transmission of (5), wherein the compound exerts an action to promote a release of brain somatostatin through suppression of a negative feedback mechanism of brain somatostatin release.

(7) The method for expressing long-term potentiation of synaptic transmission of (5) or (6), which is a method for the prophylaxis or treatment of cerebral diseases.

(8) The method for expressing long-term potentiation of synaptic transmission of (5) or (6), which is a method for the prophylaxis and/or treatment of dementia or amnesia (9) Use of a compound having a brain somatostatin activation property for the production of an agent for the expression of long-term potentiation of synaptic transmission.

(10) The use of a compound having a brain somatostatin activation property according to (9), wherein the compound exerts an action to promote a release of brain somatostatin through suppression of a negative feedback mechanism of brain somatostatin release.

(11) The use of a compound having a brain somatostatin activation property according to (9) or (10), which is for the production of an agent for the prophylaxis and/or treatment of cerebral diseases.

(12) The use of a compound having a brain somatostatin activation property according to (9) or (10), which is for the production of an agent for the prophylaxis and/or treatment of dementia or amnesia.

(13) A method for screening an agent for expression of long-term potentiation of synaptic transmission, which comprises using a somatostatin releasing action as an index

(14) The screening method of (13), which is a screening method of an anti-dementia agent or anti-amnesia agent.

(15) A method for screening an agent for expression of long-term potentiation of synaptic transmission, which comprises stimulating hippocampal slices, bringing a hippocampal slice into contact with a test compound, measuring an amount of somatostatin released from the hippocampal slice and/or a release time thereof, measuring an amount of somatostatin released from a hippocampal slice and/or a release time thereof in the absence of a contact with the test compound, and comparing the amounts and/or the times to calculate the amount of somatostatin released from the hippocampal slice and/or the release time thereof caused by the contact with the test compound.

(16) The screening method according to (15), which is a screening method of an anti-dementia agent or anti-amnesia agent.

(17) The agent for expression of long-term potentiation of synaptic transmission of (1), wherein the compound having the brain somatostatin activation property is a compound obtained by the screening method of any of (13) to (16).

(18) The method for expressing long-term potentiation of synaptic transmission according to (5), wherein the compound having the brain somatostatin activation property is a compound obtained by the screening method of any of (13) to (16).

(19) The use of a compound having a brain somatostatin activation property according to (9), wherein the compound having the brain somatostatin activation property is obtained by the screening method of any of (13) to (16).

(20) A compound selected by the screening method described in any of (13) to (16).

DETAILED DESCRIPTION OF THE INVENTION

Figure 1:
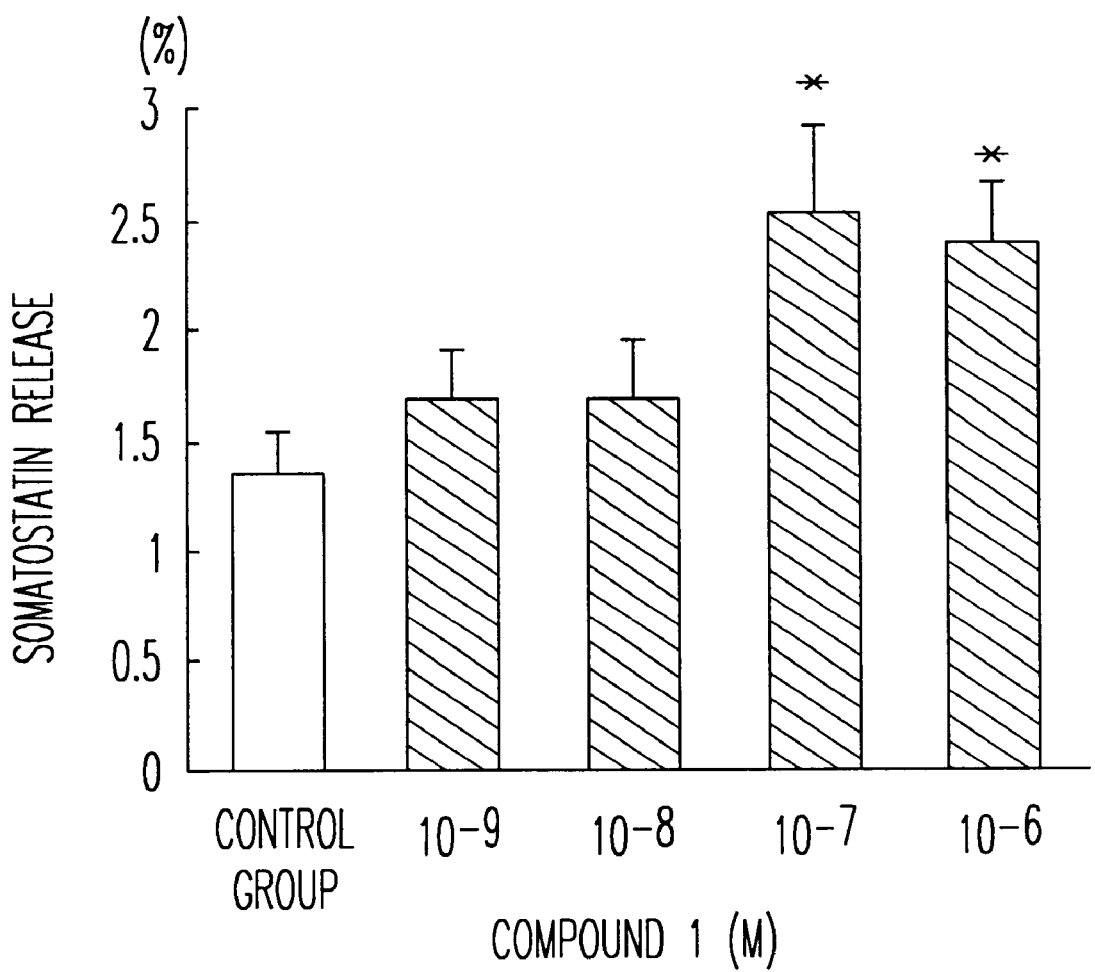
FIG. 1 is a bar graph showing the action of compound 1 to be mentioned later, i.e., N-(4-acetyl-1-piperazinyl)-p-fluorobenzamide monohydrate, on somatostatin release from rat hippocampal slice upon stimulation with 50 mM $K^+$, wherein the axis of ordinate is somatostatin release (%) and each value is mean± S.E.M (n=10–11). The symbol * means that Dunnett's multiple comparison test showed a significant difference by P<0.05 of the group containing various concentrations of compound 1 as compared to the control group.

Respective definitions and specific examples thereof used in the present invention, as well as preferable embodiments thereof are explained in detail in the following.

Compound having brain somatostatin activation property:

The activation property of brain somatostatin means, for example, an action to promote release of brain somatostatin, an action to increase biosynthesis of somatostatin within nerve cells, an action to activate somatostatin receptors, an action to potentiate expression of somatostatin property, an action to potentiate somatostatin signal transduction and the like.

The compound to be used in the present invention is one capable of activating brain somatostatin based on at least one of the aforementioned properties. Particularly, a compound having a brain somatostatin release promoting property is preferably used, which is preferably a compound that shows a brain somatostatin release promoting property through suppression of the negative feedback mechanism of brain somatostatin release.

Examples of promotion of release of brain somatostatin include actions of, for example, suppression of a negative feedback mechanism of brain somatostatin release, release of suppression by somatostatin of voltage-dependent calcium channel present in neuron, promotion of the voltage-dependent calcium channel, modification of mutual intracellular action between G protein and calcium channel, phosphorylation of calcium channel, modification of $K^+$ channel, influencing kinetic behavior of somatostatin-containing vesicle, and the like, whereby release of somatostatin is promoted.

The action to increase biosynthesis of somatostatin in the nerve cells may be, for example, an action to potentiate the expression of somatostatin mRNA, an action to promote protein synthesis from mRNA, or an action to promote cleaving out from the precursor of somatostatin, wherein these actions promote the release of brain somatostatin.

The brain somatostatin release promoting property is evaluated by the method to be mentioned later.

The action to activate somatostatin receptors may be, for example, the actions to stimulate somatostatin receptors, to suppress desensitization of somatostatin receptors, to suppress intracellular transfer of somatostatin receptors, to increase the number of somatostatin receptors present in the postsynaptic membrane and the like.

The action to potentiate the expression of somatostatin property may be, for example, an action to suppress the decomposition of somatostatin, an action to suppress the re-uptake of somatostatin and the like.

The action to potentiate the signal transmission of somatostatin is exemplified by an action to potentiate G protein, cAMP, protein kinase, protein phosphatase, transcription factor and the like, coupled with a somatostatin receptor, wherein the action is directed to an intracellular signal transduction messenger and the like other than somatostatin receptor, thereby to potentiate the signal transduction of somatostatin.

The compound having a brain somatostatin activation property to be used in the present invention encompasses any compound having such an activation property. Preferable examples thereof include compounds of the following formulas:

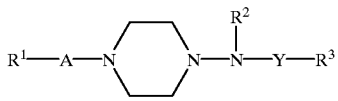

(I)

wherein R¹ is lower alkyl, aryl, ar(lower)alkoxy or heterocyclic group, each of which may be substituted with halogen, R² is hydrogen atom or lower alkyl, R³ is cyclo(lower)alkyl, aryl or ar(lower)alkyl, each of which may be substituted with halogen, A is —CO—, —SO₂— or lower alkylene, and Y is —CO—, —SO₂— or —CONH— (EP Publication No. 436734), particularly, N-(4-acetyl-1-piperazinyl)-p-fluorobenzamide monohydrate (compound 1) (International Publication No. WO98/25914), and

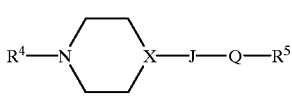

(II)

wherein R⁴ is acyl, R⁵ is aryl, arylamino or aryloxy, the aryl moiety of all of which may be substituted by halogen; pyridyl or pyridylamino; X is CH or N, J is a single bond, lower alkylene or

wherein R⁶ is hydrogen, lower alkyl or N-protective group, Q is —CH₂—, —CO— or —SO₂—, provided that when X is N, J is a single bond or lower alkylene, particularly, N-(1-acetylpiperidin-4-yl)-4-fluorobenzamide.

With regard to the brain somatostatin release promoting property, the brain somatostatin release promoting property is said to be expressed and the compound is said to have a brain somatostatin activation property, when the release amount of somatostatin by depolarization stimulation is increased due to a pretreatment of a hippocampal slice with a certain compound, as compared to when the pretreatment with the compound is void.

With regard to the property of increasing biosynthesis of somatostatin, the property of increasing biosynthesis of somatostatin in nerve cells is said to be expressed and the compound is said to have a brain somatostatin activation property, when a somatostatin content of the nerve cells is increased in the nerve cells due to a pretreatment with a certain compound, as compared to when the pretreatment with the compound is void.

With regard to the somatostatin receptor activation property, the somatostatin receptor activation property is said to be expressed and the compound is said to have a brain somatostatin activation property, when binding of somatostatin labeled with a radioisotope (e.g., $^{125}$I and the like) to a somatostatin receptor in the nerve cells decreases due to a pretreatment with a certain compound, as compared to when the pretreatment with the compound is void.

With regard to the potentiation property of the expression of somatostatin property, the potentiation property of the expression of somatostatin property is said to be expressed and the compound is said to have a brain somatostatin activation property, when the activity of somatostatin degrading enzyme in the nerve cells is suppressed due to a pretreatment with a certain compound, as compared to when the pretreatment with the compound is void.

With regard to the potentiation property of the somatostatin signal transmission, the potentiation property of the somatostatin signal transmission is said to be expressed and the compound is said to have a brain somatostatin activation property, when the amount of intracellular phosphorylated protein in the nerve cells changes due to a pretreatment with a certain compound, as compared to when the pretreatment with the compound is void.

With regard to the property of suppressing the negative feedback mechanism of brain somatostatin release, the property of suppressing the negative feedback mechanism of brain somatostatin release is said to be expressed and the compound is said to have a brain somatostatin release promoting property, when the suppressive action on the membrane potential dependent calcium current by somatostatin in the hippocampus pyramidal cells is released due to a pretreatment with a certain compound. Agent for expression of long-term potentiation of synaptic transmission:

The compound having a brain somatostatin activation property expresses the long-term potentiation of synaptic transmission.

Therefore, this compound is used as an agent for expression of long-term potentiation of synaptic transmission for mammals such as human, dog, cow, horse, rat, guinea pig and the like.

In the present invention, an agent for expression of long-term potentiation of synaptic transmission means a compound capable of inducing potentiation of general neurotransmission efficiency after high frequency and short time stimulation and sustaining the increased transmission efficiency for a long time.

The site where the long-term potentiation of synaptic transmission is expressed is subject to no limitation as long as it is a nerve system present in the hippocampus. Examples thereof include nerve systems present in brain, such as cerebral cortex, corpus amygdaloideum and the hike, with preference given to the mossy fiber-CA3 pathway, perforant path-dentate gyros pathway and Schaffer collaterals-CA1 pathway.

The agent for expression of long-term potentiation of synaptic transmission of the present invention is effective for the prophylaxis and/or treatment of cerebral diseases such as dementia (e.g., senile dementia, Alzheimer's dementia, dementia associated with various diseases such as cerebral vascular dementia, cerebral post-traumatic dementia, dementia due to brain tumor, dementia due to chronic subdural hematoma, dementia due to normal pressure hydrocephalus, post-meningitis dementia, Parkinson's disease type dementia, and the like), amnesia, manic-depressive psychosis, schizophrenia, Parkinson's disease, psychosomatic disease, and the like, particularly for the treatment and/or treatment of dementia and amnesia The long-term potentiation of synaptic transmission is evaluated according to the following criteria.

In a long-term potentiation phenomenon observed in the hippocampus of an animal, namely, guinea pig, which is observed according to the method conventionally known (Matsuoka et al., *Brain Research*, vol. 553, p. 188, 1991), when a pretreatment of hippocampus with a certain compound (bringing hippocampus into contact with the compound) leads to the augmentation of LTP, after tetanic stimulation, of potential generated from the CA3 field pyramidal cell caused by stimulation of mossy fiber to not less than 1200%, preferably not less than 140%, more preferably not less than 160%, still more preferably not less than 180%, most preferably not less than 2000%, when that without the pretreatment with the compound is 100%, the long-term potentiation of synaptic transmission is said to be expressed, and this compound can be said to be an agent for expression of long-term potentiation of synaptic transmission.

Alternatively, in a long-term potentiating phenomenon observed in the hippocampus of an animal, namely, guinea pig, which is observed according to the method conventionally known (Matsuoka et al., *Brain Research*, vol. 553, p. 188, 1991), when a long-term potentiation phenomenon is expressed in a sustained manner for not less than 10 minutes, preferably not less than 20 minutes, more preferably not less than 30 minutes, most preferably not less than 60 minutes due to a pretreatment with a certain compound, a long-term potentiation of synaptic transmission is said to be expressed and this compound can be said to be an agent for expression of long-term potentiation of synaptic transmission.

Note that variations in numerical values to the degree that those of ordinary skill in the art consider substantially the same statistically as the above-mentioned numerical values should be construed as corresponding to the above-mentioned numerical values.

As used herein, the pretreatment with a certain compound can be conducted by, for example, immersing the compound generally for 25 minutes in an outer solution containing hippocampus therein, and removing the compound by a method such as washing.

The test method for the evaluation of the above-mentioned long-term potentiation of synaptic transmission may be a method conventionally known or a method analogous thereto, with preference given to the following method.

Round slices are prepared from the hippocampus removed from an animal, for example, guinea pig. The slices are 500 $\mu$m in thickness. Each slice is placed in a container such as a perfusion chamber and the population spikes are extracellularly recorded in the following manner while perfusing with an artificial cerebrospinal fluid at 33–34° C. at a flow rate of 1.8–2.0 ml/min.

At this time, the test compound is added to the perfusate so that the concentration of the test compound in each container would be a serially diluted concentration, and the test compound is applied to the hippocampal slices from 21 minutes before the tetanic stimulation to 4 minutes thereafter.

The artificial cerebrospinal fluid to be used here is exemplified by those used in the screening method in the present invention to be mentioned later.

Mossy fiber is stimulated with a stimulation electrode at a voltage of not more than 10 V, frequency of 0.2 Hz, and the population spikes in the CA3 field pyramidal cell layer are recorded every 5 minutes. When the population spikes to be recorded are stabilized, tetanic stimulation is applied for the induction of LTP. The tetanic stimulation includes stimulation at the same voltage and a frequency of 33 Hz for 5 seconds. The height of from the negative peak to the next positive peak of the obtained population spikes after stimulation is measured and taken as an amplitude of population spikes. The degree of LTP can be expressed by a potential variation (%) showing an increase in the amplitude of population spikes after tetanic stimulation relative to the average of 4 measurements of the amplitudes of population spikes before tetanic stimulation. As the index of the property of a drug, the area in the graph of time lapse versus potential variation, between the graph from 12 minutes to 62 minutes after tetanic stimulation and the line where the potential variation is 0%, may be calculated and taken as the magnitude of LTP.

Each value of the potential variation and the magnitude of LTP which is calculated based on the potential variation as mentioned above is subjected to one-way analysis of variance and Dunnett's multiple comparison test, and compared based on the above-mentioned evaluation criteria, whereby the long-term potentiation of synaptic transmission can be evaluated.

Screening Method

The screening method of the present invention comprises screening of the test compound to be screened (hereinafter to be abbreviated as a test compound) using the somatostatin releasing property as an index.

The screening method of the agent for expression of long-term potentiation of synaptic transmission of the present invention, particularly, an anti-dementia agent and an anti-amnesia agent, is a selection method of the test compound characteristically comprising bringing human or animal nerve cells into contact with a test compound, measuring an amount of somatostatin released from the nerve cells and a release time thereof, measuring an amount of somatostatin released from the nerve cells and a release time thereof in the absence of a contact with the test compound, and comparing the amounts and the times to measure the amount of somatostatin released from the nerve cells and the release time thereof caused by the contact with the test compound.

The above-mentioned nerve cells include, for example, hippocampus, preferably hippocampal slices, primary culture nerve cell, nerve cell strain, oocyte and the like.

The contact with the test compound can be conducted by, for example, immersing the test compound for 20–120 minutes in an outer solution in which the nerve cells are immersed and removing the test compound by washing and the like.

Preferred screening method is as follows.

Hippocampal slices are prepared from an animal (e.g., rat, guinea pig, mouse and the like) by a method conventionally known or a method analogous thereto. The slices are generally 100–600 $\mu$m, preferably 300–400 $\mu$m, in thickness. While the direction of slicing is not particularly limited, they are preferably transverse slices or longitudinal slices. For example, the slices are placed in a container such as a perfusion chamber, by general 30 slices, more preferably 20 slices, and perfused with an artificial cerebrospinal fluid while incubating at generally 20–37° C., preferably 36–37° C. The perfusate is exchanged every 5–20 minutes, preferably 10–15 minutes. Fractions are obtained from each cycle, which step is repeated 10 to 20 times, preferably 15 times. While repeatedly obtaining the fractions, the test compound is added to the perfusate to serially diluted concentrations that are within the range of preferably $10^{-10}$–$10^{-5}$ M, more preferably $10^{-9}$–$10^{-6}$ M, whereby fractions containing the test compound at respective concentrations are obtained. The test compound is immersed in perfusate for generally 20–120 minutes, preferably 80 minutes.

Generally 0–60 minutes, preferably 10–30 minutes, after the addition of the test compound, stimulation is preferably added. The stimulation is applied for generally 5–20 minutes, preferably 10–15 minutes. It is important that the stimulation be applied after the addition of the test compound, but the stimulation may be applied while the test compound is present in the perfusate or after the test compound is removed by washing with a perfusate.

The somatostatin in the perfusate of each fraction obtained as above is quantified according to a treatment method conventionally known (for example, perfusare is lyophilized and subjected to a radioimmunoassay). After the completion of the step for obtaining the fractions, the somatostatin remaining in hippocampal slices is extracted by a conventional method, which amount is similarly quantified.

The composition of the artificial cerebrospinal fluid to be used as the perfusate in the above-mentioned screening method can be modified as appropriate depending on the test conditions and test compound and the like to be used. Preferable composition includes the following. Artificial cerebrospinal fluid composition: NaCl, 124 mM; KCl, 5 mM; $KH_2PO_4$, 1.24 mM; $MgSO_4$, 1.3 mM; $CaCl_2$, 2.4 mM; $NaHCO_3$, 26 mM; D-glucose, 10 mM This perfusate is used with saturation with a mixed gas of oxygen and carbon dioxide, such as a mixed gas of oxygen (95%) and carbon dioxide (5%), typically used for pharmacological experiments.

The above-mentioned screening method may be modified as necessary.

The amount of somatostatin quantified is compared with the amount when the contact with the test compound is void, based on the following criteria, whereby the somatostatin release promoting property of the test compound can be evaluated.

The screening method of the present invention is preferably conducted under stimulation as mentioned above. Such stimulation is a model of a specific stimulation related to learning or tetanic stimulation. The stimulation is not particularly limited as long as the nerve cells present in the hippocampal slice are exited. Specific examples thereof include stimulation by potassium ion, electric stimulation, depolarization stimulation, stimulation with a drug and the like. When a mere addition of the test compound does not lead to the somatostatin release property and the test compound shows somatostatin release property only upon stimulation, it can be a confirmation that the nerve cells are free from influence of this test compound as long as no stimulation is involved, thus ensuring the safety of this compound.

The somatostatin release property is evaluated based on the following criteria.

In the screening method of the present invention, when the somatostatin release amount due to the contact with the test compound increases by not less than 100/, preferably not less than 20%, more preferably not less than 30%, still more preferably not less than 40%, most preferably not less than 50%, as compared to the release amount when the contact with the test compound is void (which is taken as 100%), the test compound is said to have a somatostatin release promoting property. It is preferable that the somatostatin release amount upon stimulation mentioned above be evaluated according to the above-mentioned criteria It is appreciated that variations in numerical values to the degree that those of ordinary skill in the art consider substantially the same statistically as the above-mentioned numerical values should be construed as corresponding to the above-mentioned numerical values The test compound to be subject to the screening in the present invention is free of any particular limitation and may be selected from natural product, chemically synthesized compound, nucleic acid, peptide, antibody and the like obtained by genetic engineering and their libraries. The test compound is preferably a pure substance, but may be a mixture or racemic compound. The test compound may be also modified to label with radioisotope or may contain modification made during construction of library. The obtained test compound can be optimized by chemical synthetic method and the like.

By selecting the test compounds using the screening method of the present invention, an agent for expression of long-term potentiating of synaptic transmission, particularly an anti-dementia agent, an anti-amnesia agent and the like can be screened.

The test compound selected by the screening method of the present invention and a compound obtained by optimizing this compound are all encompassed in the scope of the present invention.

The compound of the present invention having a brain somatostatin activation property can be used in the dosage form of a solid, semi-solid or liquid preparation in conjunction with organic or inorganic carrier or excipient, which is suitable for rectal administration, pulmonary (pernasal or buckle inhalation), nasal drop, eye drop, external Focal), oral or parenteral (subcutaneous, intravenous or intramuscular) administration and the like, direct administration to diseased region, such as brain, spinal fluid, cerebroventricle and the like, or inhalation.

A compound having a brain somatostatin activation property can be admixed with pharmaceutically acceptable substantially non-toxic carrier or excipient conventionally used for dosage forms suitable for use, such as tablets, pellets, troches, capsules, suppositories, cream, ointment, aerosol, inhalable powder medicine, liquid, emulsion, suspension, and the like. Where necessary, auxiliary, stabilizer, tackifier, coloring agent and flavor can be used.

The agent for the expression of long-term potentiation of synaptic transmission, particularly an anti-dementia agent and an anti-amnesia agent, of the present invention can be produced by a method conventionally used in the pertinent field. Where necessary, a method routinely used in this technical field can be used for the production of these drugs for an improved bioavailability.

The agent for the expression of long-term potentiation of synaptic transmission, particularly an anti-dementia agent and an anti-amnesia agent, of the present invention is preferably administered intravenously (inclusive of addition into infusion), intramuscularly or orally when applying to humans or animals.

The agent for the expression of long-term potentiation of synaptic transmission, particularly an anti-dementia agent and an anti-amnesia agent, of the present invention is contained in a preparation in an amount sufficient to provide a desired prophylactic and/or treatment effect on the progression and conditions of diseases.

The amount and administration route of the compound having a brain somatostatin activation property are subject to variation depending on the kind of compound, age and conditions of the patients to be the subject of the prophylaxis and/or treatment. When compound 1 is used, for example, the daily dose is 0.1–10 mg/kg body weight by oral administration, which is given once to several times a day for the treatment and/or prophylaxis of the aforementioned diseases.

The present invention is explained in more detail in the following by way of Examples which do not limit the present invention.

EXAMPLES

Experimental Example 1

Effect of Compound 1 on Somatostatin Release From Rat Hippocampal Slice (1) Method Rat hippocampal slices (thickness 350 µm, round slice) were prepared by a standard method. Twenty rat hippocampal slices were placed in a perfusion chamber, incubated at 37° C. and perfused by a batch method while exchanging the incubation buffer every 10 minutes. The incubation buffer used had the composition as noted below. A mixed gas of oxygen (95%) and carbon dioxide (5%) was used to saturate the buffer.

Composition of incubation buffer. NaCl, 124 mM; KCl, 5 mM; $KH_2PO_4$, 1.24 mM; $MgSO_4$, 1.3 mM; $CaCl_2$, 2.4 mM; $NaHCO_3$, 26 mM; D-glucose, 10 mM Perfusion for 150 minutes gave fractions 1–15. To fraction 9 was applied a high $K^+$(50 mM) stimulation. Compound 1 was added to fractions 7–15 to the concentration of $10^{-9}$ M, $10^{-7}$ M, $10^{-7}$ M, $10^{-6}$ M, respectively. Nothing was added to control group. The respective fractions thus obtained were concentrated by lyophilization and somatostatin in the perfusate was quantified by radioimmunoassay (RIA). After the completion of the experiment, somatostatin remaining in the slices was extracted by a conventional method and quantified by radioimmunoassay. The somatostatin amount released by high $K^+$ (50 mM) stimulation was calculated and the amount of somatostatin released due to the property of compound 1 was measured.

Somatostatin release (%) by compound 1 at each concentration was calculated as in the following. The somatostatin amount of each fraction was expressed by the percentage (%) relative to the somatostatin residual amount at the time the fraction was obtained. The value of fraction 8 immediately before high $K^+$ (50 mM) stimulation was taken as the base and the values exceeding the base value were added with regard to fraction 9 and the subsequent peak fractions exceeding the base value to give somatostatin release (%). The number of the test samples measured was 10 or 11. Each value (%) was expressed by mean±S.E.M. The property of compound 1 was subjected to Dunnett's multiple comparison test relative to control group.

(2) Result

The results are shown in FIG. 1. The compound 1 promoted somatostatin release when stimulated at high K+ (50 mM), and the property was significant at $10^{-7}$ M and $10^{-6}$ M. The concentration dependency was similar to the long-term potentiation in Experimental Example 2 to be mentioned later. By the use of the screening method of the present invention, compound 1 was shown to have a somatostatin release promoting property on hippocampus.

Experimental Example 2
Effect of Compound 1 on LTP in Mossy Fiber-CA3 Field Pyramidal Cell of Hippocampal Slice
(1) Method Slices (thickness 500 μm, round slice) were prepared from hippocampus removed from male Hartley guinea pigs (body weight 220–350 g) and population spikes were extracellularly recorded. The hippocampal slices were perfused with an artificial cerebrospinal fluid (33–34° C., composition: NaCl, 124 mM; KCl, 5 mM; $KH_2PO_4$, 1.24 mM; $MgSO_4$, 1.3 mM; $CaCl_2$, 2.4 mM; $NaHCO_3$, 26 mM; D-glucose, 10 mM) saturated with a mixed gas of oxygen (95%) and carbon dioxide (5%) at flow rate of 1.8–2.0 ml/min. Mossy fiber was stimulated with a stimulating electrode at a voltage of not more than 10 V, frequency of 0.2 Hz and the population spikes in the CA3 field pyramidal cell layer was recorded every 5 minutes. When the population spikes to be recorded were stabilized, tetanic stimulation for induction of LTP was applied. The tetanic stimulation includes stimulation at the same voltage of not more than 10 V, as when the stimulation was applied at a frequency of 0.2 Hz, but upon increase of the frequency to 33 Hz for 5 seconds. The height of from negative peak to the next positive peak of the obtained population spikes after stimulation was measured and taken as an amplitude (population spike amplitude;PSA). The degree of LTP was expressed by a potential variation (%) by the increase in the amplitude of population spikes after tetanic stimulation relative to the average of 4 measurements of the amplitudes of population spikes obtained before tetanic stimulation. Each value was expressed by mean±S.E.M (the number of slices tested was 3 to 8). As the index of the property of a drug, the area (%·min) between the graph from 12 minutes to 62 minutes after tetanic stimulation and the line where the potential variation is 0%, in the time lapse graph of potential variation, was calculated and taken as the magnitude of LTP. Compound 1 was dissolved in and diluted with distilled water and added to perfusate to the concentration of $10^{-9}$ M, $10^{-8}$ M, $10^{-7}$ M and $10^{-6}$ M, respectively, and applied to a hippocampal slice for 25 minutes from 2 minutes before the tetanic stimulation to 4 minutes thereafter. Nothing was added to perfusate for control group.

The property of compound 1 relative to the magnitude of LTP was tested by one-way analysis of variance and Dunnett's multiple comparison test.

(2) Results

Figure 2:
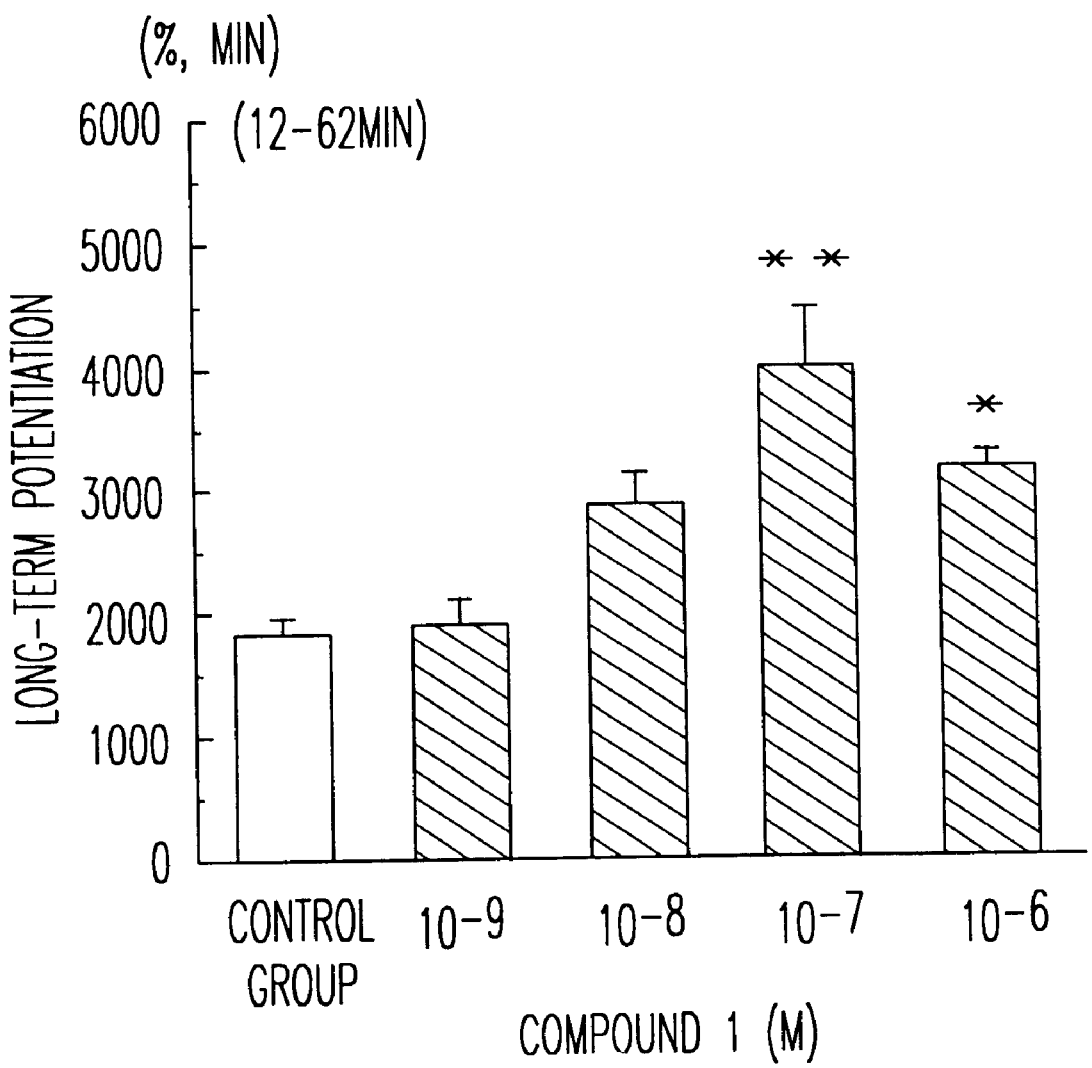
FIG. 2 is a bar graph showing the action of compound 1 on hippocampus long-term potentiation phenomenon, wherein the axis of ordinate shows the magnitude of LTP by the integral (%·min) of potential variation (%) from 12 minutes to 62 minutes after tetanic stimulation. The symbol * means that one-way analysis of variance and Dunnett's multiple comparison test showed a significant difference by P<0.05 of the group containing various concentrations of compound 1 as compared to the control group. The symbol**means that one-way analysis of variance and Dunnett's multiple comparison test showed a significant difference by P<0.01 of the group containing various concentrations of compound 1 as compared to the control group.

From the potential variation with the lapse of time, compound 1 was found to have shown no significant influence of the response of base before tetanic stimulation. As is can be seen from FIG. 2 showing the magnitude of LTP, compound 1 increased potential variation after tetanic stimulation at $10^{-7}$ M and $10^{-6}$ M, wherein its action was maximal at $10^{-7}$ M. From the foregoing, it was shown that compound 1 had a promoting property specific to the mechanism necessary for the occurrence of phenomenon of long-term potentiation of synaptic transmission after tetanic stimulation.

The hippocampal slice obtained from the guinea pig treated with cysteamine (200 mg/kg) did not show LTP enhancing property by compound 1 at $10^{-7}$ M. This reveals that hippocampus endogeneous somatostatin activation property is involved in the LTP enhancing property by compound 1.

Experimental Example 3

Effect of Compound 1 on Voltage-dependent $Ca^{2+}$ Current of Rat Hippocampus Pyramidal Cell (1) Method Hippocampal slices were prepared from the brains of 5- to 14-day-old male Wistar rats and the nerve cells were quickly isolated by trypsin enzyme treatment method. According to the whole cell patch-clamp method, the membrane potential of hippocampus pyramidal cell was fixed at −80 mV and the membrane potential-dependent potassium current (Ica) was measured in $Cs^+$ electrode inner solution and $Ba^{2+}$ bath outer solution. The resistance of the electrode was 2–4 MΩ. Compound 1 was added to bath outer solution concentrations of 0.01 μM, 0.1 μM and 1.0 μM, respectively, and perfused with the bath outer solution. Nothing was added to the bath outer solution for the control group. The maximal value of the current (peak amplitude) was measured, and calculated as the variation (%) relative to the value before addition of compound 1. Each value (%) was expressed by mean±S.E.M. The number of measurements was 7. The property of compound 1 was evaluated by Dunnett's multiple comparison test relative to the control group.

(2) Result

Figure 3:
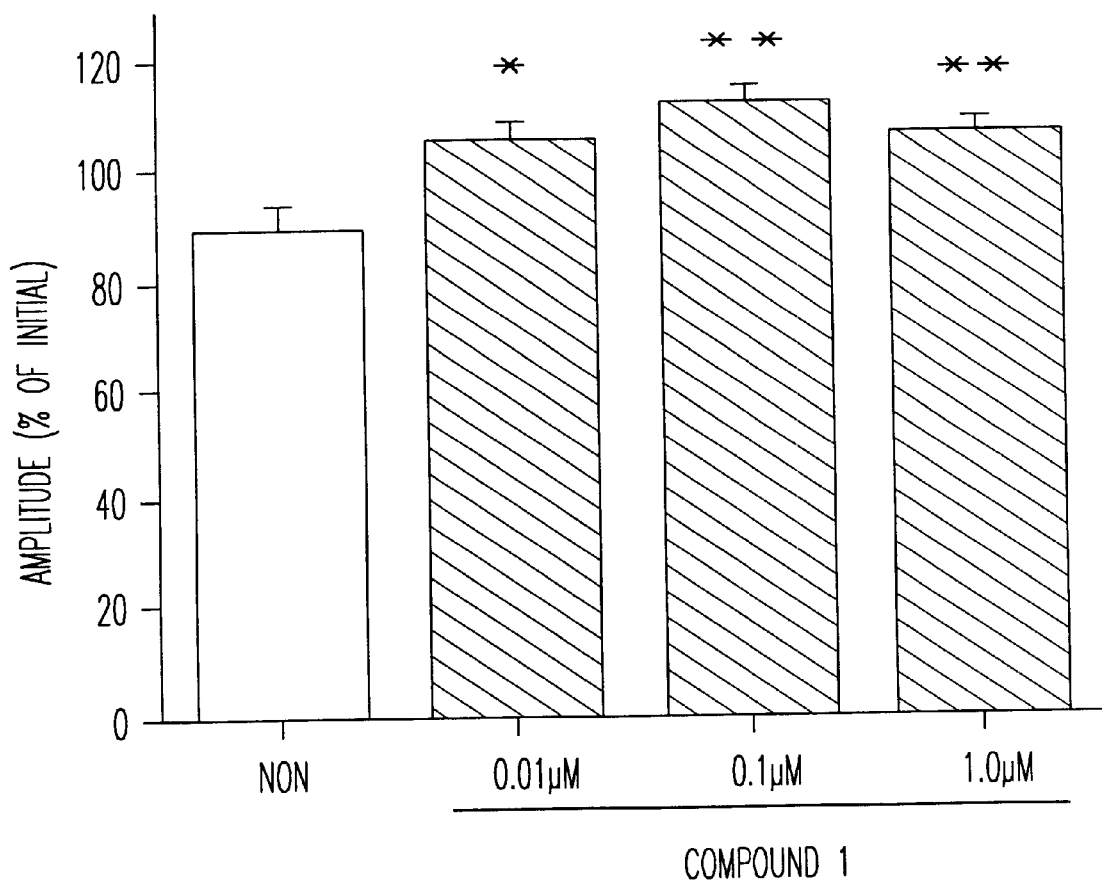
FIG. 3 is a bar graph showing the dose-response dependency of compound 1 with regard to voltage-dependent calcium channel, wherein the axis of ordinate shows variation (%) of the maximal value of the membrane potential dependent calcium current to the value before the addition of compound 1, wherein each value is meant±S.E.M (n=7). The symbol*means that Dunnett's multiple comparison test showed a significant difference by P<0.05 of the group containing various concentrations of compound 1 as compared to the control group. The symbol**means that Dunnett's multiple comparison test showed a significant difference by P<0.0 1 of the group containing various concentrations of compound 1 as compared to the control group.

The results are shown in FIG. 3. Compound 1 significantly promoted membrane potential-dependent calcium current at concentrations of 0.01 μM, 0.1 μM and 1.0 μM as compared to the control group, and showed bell-shape dose dependency. Therefore, compound 1 was shown to have a promoting action on the voltage-dependent calcium channel of hippocampus pyramidal cells.

Experimental Example 4

Effect of Somatostatin and Compound 1 on Voltage-dependent $Ca^{2+}$ Current of Rat Hippocampus Pyramidal Cell (1) Method In the same manner as in Experimental Example 3 except that compound 1 and somatostatin were added in such a manner that the concentration of somatostatin in the bath outer solution was $10^{-7}$ M when somatostatin alone was added, and the concentration of compound 1 in the bath outer solution was $10^{-7}$ M and the concentration of somatostatin in the bath outer solution was $10^{-7}$ M when both compound 1 and somatostatin were added, the experiment was conducted. Nothing was added to the control group. The maximal value of each current was measured, and calculated as the variation (%) to that prior to addition. Each value (%) was expressed by mean±S.E.M. The number of measurements of the group added with somatostatin was 11 and that of the group added with both compound 1 and somatostatin was 7. The both groups were subjected to Dunnett's multiple comparison test.

(2) Result

Figure 4:
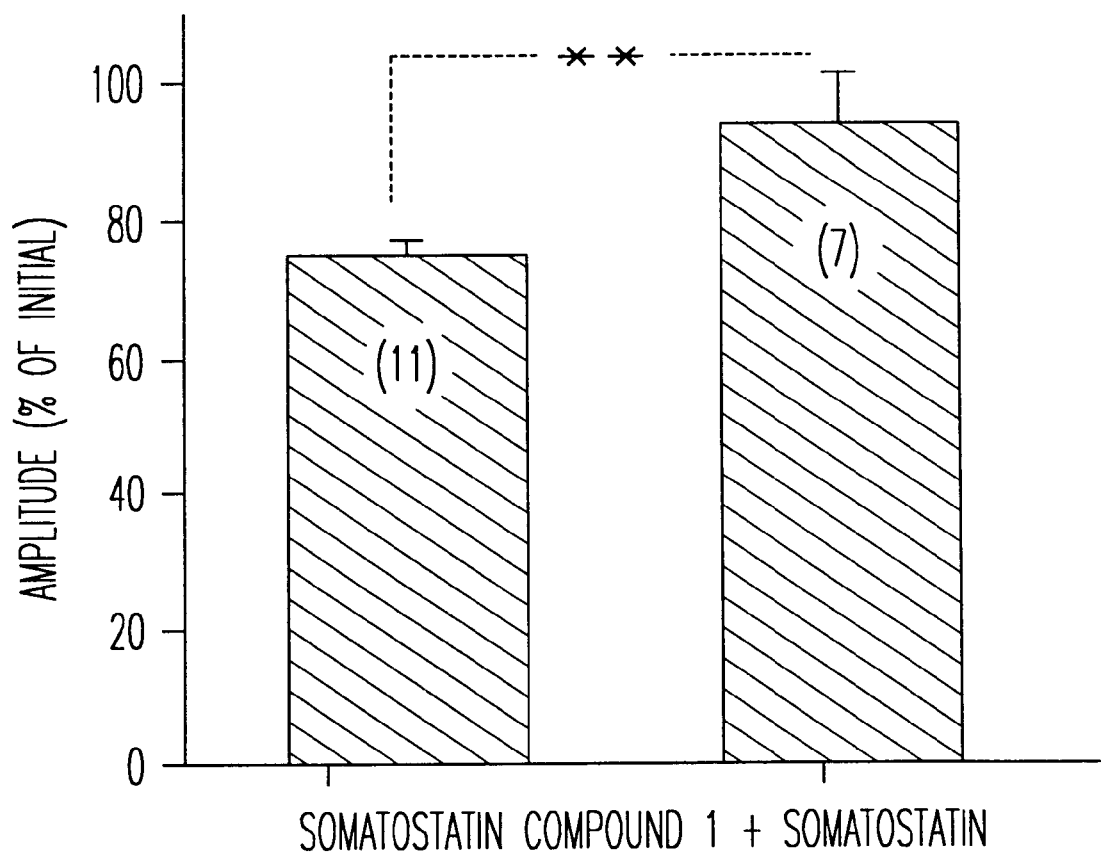
FIG. 4 is a bar graph showing the action of somatostatin and compound 1 on the membrane potential dependent calcium current, wherein the axis of ordinate shows variation (%o) of the maximal value of the membrane potential dependent calcium current upon addition of somatostatin alone or both compound 1 and somatostatin, to the value before addition of somatostatin alone or both compounds and somatostatin and each value is mean±S.E.M., and the numerals in parentheses are the number of times of measurements. The symbol means that Dunnett's multiple comparison test showed a significant difference by P<0.01 of the group containing compound 1 and somatostatin as compared to the group containing somatostatin.

The results are shown in FIG. 4. While somatostatin evidently suppressed membrane potential-dependent calcium current, suppressive property of somatostatin was completely released in the presence of compound 1. Hence, compound 1 was shown to release the suppressive property of somatostatin on the voltage-dependent calcium channel of hippocampus pyramidal cell and has a promoting property. From the results of Experimental Example 3 and this Experimental Example, compound 1 was shown to suppress the negative feedback mechanism of brain somatostatin release.

What is claimed is:

1. A method for expressing long-term potentiation of synaptic transmission, comprising:
   administering to a tissue in need thereof, an effective amount of a compound exerting an action to promote release of a brain somatostatin through suppression of a negative feedback mechanism of brain somatostatin release,
   with the proviso that the compound is not a compound of formula (I):

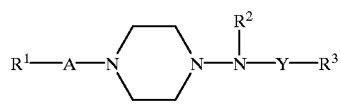

(I)

wherein $R^1$ is lower alkyl, aryl, ar(lower)alkoxy or a heterocyclic group, each of which may be substituted with halogen,
$R^2$ is a hydrogen atom or lower alkyl,
$R^3$ is cyclo(lower)alkyl, aryl or ar(lower)alkyl, each of which may be substituted with halogen,
A is —CO—, —SO$_2$— or lower alkylene, and
Y is —CO—, —SO$_2$— or —CONH—.

2. The method of claim 1, wherein said compound is administered to a subject in need of prophylaxis or treatment of cerebral disease.

3. The method of claim 1, wherein said compound is administered to a subject in need of prophylaxis or treatment of dementia or amnesia.

4. A method for identifying a compound suppressing the negative feedback mechanism of brain somatostatin release, comprising:
   contacting a nerve cell sample with somatostatin, and a second nerve cell sample with somatostatin and said compound,
   comparing membrane potential-dependent calcium current of the cell sample contacted with somatostatin, with the membrane potential-dependent calcium current of the second cell sample contacted with somatostatin and said compound,
   and selecting a compound which decreases the suppressive effect of somatostatin on said membrane potential-dependent calcium current, thereby identifying a compound suppressing the negative feedback mechanism of brain somatostatin release.

5. The method of claim 4, wherein said compound is not a compound of the formula:

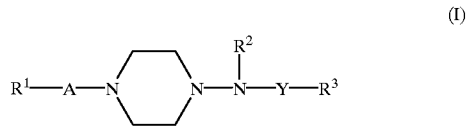

(I)

wherein $R^1$ is lower alkyl, aryl, ar(lower)alkoxy or a heterocyclic group, each of which may be substituted with halogen,
$R^2$ is a hydrogen atom or lower alkyl,
$R^3$ is cyclo(lower)alkyl, aryl or ar(lower)alkyl, each of which may be substituted with halogen,
A is —CO—, —SO$_2$— or lower alkylene, and
Y is —CO—, —SO$_2$— or —CONH—.

6. A method for the prophylaxis or treatment of cerebral diseases comprising:
   administering an effective amount of a compound obtained by the method of claim 5.

7. A method for the prophylaxis or treatment of dementia or amnesia comprising:
   administering an effective amount of a compound obtained by the method of claim 5.

8. The method according to claim 4 further comprising screening said compound for an ability to provide prophylaxis or treatment for dementia or amnesia.

9. A method for expressing long-term potentiation of synaptic transmission, comprising:

the step of administering to a tissue in need thereof, a means for exerting an action to promote release of a brain somatostatin through suppression of a negative feedback mechanism of the brain somatostatin release, with the proviso that said means is not a compound of formula (I):

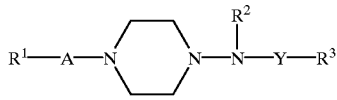
(I)

wherein $R^1$ is lower alkyl, aryl, ar(lower)alkoxy or a heterocyclic group, each of which may be substituted with halogen, $R^2$ is a hydrogen atom or lower alkyl, $R^3$ is cyclo(lower)alkyl, aryl or ar(lower)alkyl, each of which may be substituted with halogen, A is —CO—, —SO$_2$— or lower alkylene, and Y is —CO—, —SO$_2$— or —CONH—.

10. A method for identifying a compound expressing long-term potentiation of synaptic transmission, comprising:

the step of subjecting said compound to a means for determining whether said compound suppresses the negative feedback mechanism of brain somatostatin release, and the step of selecting a compound which suppresses the negative feedback mechanism of brain somatostatin release thereby identifying a compound expressing long-term potentiation of synaptic transmission.

* * * * *